United States Patent [19]

Seno et al.

[11] Patent Number: 4,604,349

[45] Date of Patent: Aug. 5, 1986

[54] PROCESS FOR PREPARING URIDINE DIPHOSPHATE-N-ACETYLGALACTOSAMINE

[75] Inventors: Taiko Seno, Osaka; Yasuto Okubo, Nara; Masao Kawamura, Akashi; Seiichi Akutsu, Kakogawa; Hirosuke Fukuda, Himeji, all of Japan

[73] Assignee: Seitetsu Kagaku Co., Ltd., Miyanishi, Japan

[21] Appl. No.: 705,217

[22] Filed: Feb. 25, 1985

Related U.S. Application Data

[62] Division of Ser. No. 499,919, Jun. 1, 1983, Pat. No. 4,569,909.

[30] Foreign Application Priority Data

| Jun. 3, 1982 | [JP] | Japan | 57-95984 |
| Jun. 3, 1982 | [JP] | Japan | 57-95986 |
| Jun. 3, 1982 | [JP] | Japan | 57-95987 |
| Jun. 3, 1982 | [JP] | Japan | 57-95988 |

[51] Int. Cl.$^4$ .................................. C12Q 1/60
[52] U.S. Cl. .................................. 435/15; 424/11
[58] Field of Search ............... 435/4, 15, 29, 34; 424/11

[56] References Cited

PUBLICATIONS

Agricultural and Biological Chemistry, vol. 37(7), 1741–1743, (1973).
Methods in Enzymology, vol. 28, 1972, pp. 511–514; 655–657.

*Primary Examiner*—Lionel M. Shapiro
*Attorney, Agent, or Firm*—Bucknam and Archer

[57] ABSTRACT

A process for preparing uridine diphosphate-N-acetylgalactosamine, which comprises treating a reaction solution obtained by the enzymatic conversion of uridine diphosphate-N-acetylglucosamine to uridine diphosphate-N-acetylgalactosamine, with uridine diphosphate-N-acetylglucosamine pyrophosphorylase to decompose the remaining uridine diphosphate-N-acetylglucosamine in the solution and then separating therefrom the uridine diphosphate-N-acetylgalactosamine for purification. In one aspect of this invention, it relates to a method for measuring the activity of α-N-acetylgalactosaminyl transferase characterized by the use of said reaction solution as the substrate for the transferase.

2 Claims, No Drawings

PROCESS FOR PREPARING URIDINE DIPHOSPHATE-N-ACETYLGALACTOSAMINE

This is a divisional of application Ser. No. 499,919, filed June 1, 1983, now U.S. Pat. No. 4,569,909.

This invention relates to a process for the preparation of uridine diphosphate-N-acetylgalactosamine (hereinafter referred to as "UDPGalNAc") and more particularly to a process for the separation and purification of UDPGalNAc comprising enzymatically converting uridine diphosphate-N-acetylglucosamine (hereinafter referred to as "UDPGlcNAc") in the presence of epimerase to UDPGalNAc thereby obtaining a reaction solution, subjecting the thus obtained reaction solution to the action of uridine diphosphate-N-acetylglucosamine pyrophosphorylase to decompose the remaining UDPGlcNAc in the reaction solution and then separating and recovering the UDPGalNAc therefrom. The invention further relates to a method for measuring the activity of glycosyl transferase, characterized by directly using a reaction solution obtained by the enzymatic conversion of UDPGlcNAc to UDPGalNAc as the substrate for the following transferase at the time of measuring the activity of α-N-acetylgalactosaminyl transferase by means of the conversion of Type O red blood cells to Type A ones.

UDPGalNAc is a compound serving as a donor of N-acetylgalactosamine which is the important sugar moiety of glyco-conjugates in the biosynthesis thereof such as glycoprotein and glycolipid, and it plays an important role as a substrate for various glycosyl transferases. Further, in vitro, for the detection and identification of variant type blood which is difficult to decide its type, UDPGalNAc has been used as a substrate for measuring the activity of glycosyl transferase (A-transferase) participating in the biosynthesis of A blood group substance among A, B and O blood group substances for human beings.

As a process for the preparation of UDPGalNAc, there has heretofore been known a process for the preparation thereof by converting UDPGlcNAc to UDPGalNAc using bacterial enzyme, in addition to various kinds of organic synthesizing processes.

More particularly, it is known that UDPGalNAc is prepared by epimerizing UDPGlcNAc using cell free extracts containing UDPGlcNAc-4-epimerase. For example, Agric. Biol. Chem. 37 (7) 1741-1743 (1973) describes that the enzyme preparation can be obtained from Bacillus subtilis IFO 3007, IFO 3009 or the like.

It is known, however, that an equilibrium exists between UDPGlcNAc and UDPGalNAc in a solution thereof and that these compounds will be present in the molar ratio of about 65:35 in the solution when it has the equilibrium composition.

The use of cell free extracts according to conventional methods will raise many problems such as, for example, a very long time is taken to reach the equilibrium, an increase in amount of the extracts in attempts to shorten said time does not exhibit a remarkable effect and, on the contrary, said increase of the extracts renders the isolation of UDPGalNAc difficult. The present inventors made intensive studies of particularly the behavior of UDPGlcNAc in the cell free extracts in attempts to solve the above-mentioned problems and, as a result of their studies, they found that an enzyme preparation obtained by partially purifying a cell free extract of bacteria (Bacillus) by means of fractionation with ammonium sulfate is the most effective in the conversion of UDPGlcNAc to UDPGalNAc. The invention is thus based on this finding or discovery.

An object of this invention is to provide a process for the conversion of UDPGlcNAc to UDPGalNAc, characterized by the use of an ammonium sulfate-fractionated solution.

The use of ammonium sulfate-fractionated solution prepared according to this invention will enable the substrate concentration of UDPGlcNAc to increase to that at least twice as high as said concentration, enable the time needed to attain the equilibrium between UDPGlcNAc⇌UDPGalNAc to decrease to ½ of, or less than, the time needed in the conventional method and further enable the after-treatment burden to lessen.

The ammonium sulfate-fractionated solution containing UDPGlcNAc-4-epimerase used in this invention may be prepared as indicated below.

Strains such as Bacillus subtilis IFO 3007 and Bacillus subtilis IFO 3009, are cultivated in a suitable nutrient medium to obtain bacterial cells, suspending the thus obtained bacterial cells in a buffer solution (pH: 7.5-8.0) of Tris-hydrochloric acid-magnesium chloride-ethylenediamine tetraacetic acid, rupturing the suspended bacterial cells by subjecting to supersonic oscillation and removing the cell debris by centrifugation thereby to obtain a cell free extract, after which the thus obtained extract is incorporated with powdered ammonium sulfate to an extent that a predetermined concentration thereof is reached. The precipitate obtained at this time is removed by centrifugation and the resulting supernatant solution is further incorporated with powdered ammonium sulfate to obtain a precipitate which is then dissolved in the aforesaid buffer solution and dialyzed to obtain an ammonium sulfate-fractionated solution. Using the ammonium sulfate-fractionated solution obtaind according to this invention, the conversion of UDPGlcNAc to UDPGalNAc may satisfactorily be carried out by the use of a conventional method as illustrated below:

UDPGlcNAc, which is the substrate, is incorporated with the ammonium sulfate-fractionated solution prepared from tris-hydrochloric acid-magnesium chloride-ethylenediamine tetraacetic acid, diluted with water and incubated at a predetermined temperature for a predetermined time to obtain a reaction solution which is then boiled for several minutes to terminate the reaction and centrifuged to separate the insolubles therefrom. The remaining solution contains UDPGalNAc and UDPGlcNAc in the equilibrium ratio and may be incorporated with pyrophosphorylase to decompose the non-converted UDPGlcNAc and treated with an ion-exchange resin or the like to separate and purify the UDPGalNAc.

The concentration of UDPGlcNAc used in the conversion of UDPGlcNAc to UDPGalNAc according to this invention is in the range of 1-60 mM, preferably 5-30 mM, and the ammonium sulfate-fractionated solution used is a 20-80% saturated fraction, preferably a 40-80% saturated fraction. The reaction time is 0.5-6 hours, preferably 1-2 hours. The preferable buffer solution used is tris-hydrochloric acid-magnesium chloride-ethylenediamine tetraacetic acid and the pH thereof is usually in the range of 7.0-9.0, preferably 7.5-8.5.

According to the methods described in the previously mentioned Agric. Biol. Chem. 37, 1741-1743 (1973) and Appl. Environ. Microbiol. 41, 392-395 (1981), the separation of post-conversion UDPGalNAc from UDPGlcNAc requires an operation of decomposing the unreacted UDPGlcNAc remaining in the reaction solution by the use of UDPGlcNAc pyrophosphorylase prepared from *Staphylococcus aureus* and bakers' yeast. This operation has heretofore been performed by adsorbing and separating, with activated carbon, sugar nucleotide from the reaction solution in which the UDPGlcNAc has been treated with bacterial epimerase and then treating the nucleotide-separated solution with UDPGlcNAc pyrophosphorylase.

However, methods comprising adsorbing sugar nucleotide on activated carbon and then desorbing it with an ammoniacal ethanol solution or the like raise many problems that they are complicated to operate and a loss of 20-30% of the sugar nucleotide is unavoidable.

The present inventors made intensive studies in attempts to solve these problems and, as a result of their studies, they found that the reaction solution in which the UDPGlcNAc has been enzymatically converted to UDPGalNAc with epimerase, may be subjected directly to the action of UDPGlcNAc pyrophosphorylase without separation of the sugar nucleotide with activated carbon, thereby to decompose the UDPGlcNAc remaining in the reaction solution.

Another object of this invention is to provide an effective process for the preparation of UDPGalNAc, comprising treating a reaction solution in which the UDPGlcNAc has been enzymatically converted to UDPGalNAc in the presence of epimerase, directly with UDPGlcNAc pyrophosphorylase thereby to decompose UDPGlcNAc remaining in the reaction solution. The above process of this invention enables the subsequent reaction to start without separating the sugar nucleotide from a reaction solution in which the UDPGlcNAc has been converted. Thus, the above process is not only simplified in operational procedure but also increases the yield by 20-30%, thereby proving its great effects.

An embodiment of the present invention is summarized as follows.

UDPGlcNAc, which is the substrate, is incorporated with UDPGlcNAc-4-epimerase prepared from *B. subtilis* and a tris-HCl-MgCl$_2$-EDTA solution and to enzymatically convert the UDPGlcNAc to UDPGalNAc. The conversion reaction is suspended by boiling the whole and the precipitate produced is removed by centrifugation.

The supernatant solution so obtained is incorporated with sodium pyrophosphate, further incorporated with UDPGlcNAc pyrophosphorylase prepared from *Staphlococcus aureus* or bakers' yeast by the use of a usual method, thereby decomposing UDPGlcNAc remaining in the reaction solution into UTP and N-acetylglucosamine-1-phosphate. Thereafter, the thus decomposed solution is subjected to a usual method using ion-exchange chromatography or the like thereby to separate and purify UDPGalNAc which is the end product.

The concentration of UDPGlcNAc in the pyrophospholysis (decomposing reaction) of UDPGlcNAc according to this invention is in the range of 1-40 mM, preferably 5-20 mM, and that of sodium pyrophosphate in said pyrophospholysis is in the range of 10-200 mM, preferably 50-100 mM. The UDPGlcNAc pyrophosphorylase used in this invention may be prepared from Staphylococcus or bakers' yeast by the use of a known method. The pH of the reaction solution is in the range of 6.0-9.0, preferably 7.0-8.0, and the reaction temperature is in the range of 20°-40° C., preferably 28°-32° C.

The reaction time is in the range of about 1-20 hours, preferably 2-6 hours.

According to the previously mentioned published literature, UDPGlcNAc is enzymatically converted to UDPGalNAc thereby to obtain a mixed solution of UDPGlcNAc and UDPGalNAc, the thus obtained solution is treated with UDPGlcNAc pyrophosphorylase to decompose the UDPGlcNAc into UTP and GlcNAc-1-phosphate and the UDPGalNAc is then isolated and purified. In the conventional final step of separating UDPGalNAc, the pyrophosphorylase reaction solution is treated with activated carbon to isolate the nucleotide component therefrom, the solution so treated is subjected to chromatography using an ion-exchange resin to obtain UDPGalNAc as a fraction, the solute from the column is again treated with activated carbon to separate and purify the UDPGalNAc. However, methods comprising adsorbing the sugar nucleotide on activated carbon and the thus adsorbed nucleotide is then desorbed with an ammoniacal ethanol solution or the like, raise many problems that, for example, they are complicated in operation and a loss of sugar nucleotide is unavoidable. In addition, chromatography using an ion-exchange resin raises a problem as to yield or recovery rate. Thus, these operations greatly decrease the overall yield.

The present inventors made intensive studies in attempts to solve these problems and, as a result of their studies, they found that the separation and purification of UDPGalNAc are carried out the most effectively by paper chromatography.

A still another object of this invention is to provide a process for the effective separation and purification of UDPGalNAc which was enzymatically prepared. This process comprises enzymatically decomposing the UDPGlcNAc of a solution containing UDPGlcNAc and UDPGalNAc and then subjecting the thus treated solution to paper chromatography to separate and purify the UDPGalNAc therefrom. According to this invention, repetition of adsorption and desorption using activated carbon and a loss of UDPGalNAc due to an ion-exchange chromatography can be avoided, while UDPGalNAc can conveniently be obtained in a high yield by single operation of paper chromatography.

An embodiment of the above process is summarized as follows. A mixed solution containing UDPGlcNAc and UDPGalNAc is treated with UDPGlcNAc pyrophosphorylase to decompose the UDPGlcNAc into UTP and GlcNAc-1-phosphate. The solution so treated is boiled to suspend the reaction, the precipitate is removed by centrifugation and the supernatant solution is obtained. The supernatant solution is concentrated and incorporated with manganese chloride to precipitate pyrophosphoric acid which is then removed. The thus treated supernatant solution is further concentrated, coated in band form on filter paper and developed by a usual method. After the end of developing, the filter paper absorbs ultraviolet rays to detect the UDPGalNAc portion thereon. The said portion is cut off from the filter paper and extracted with water to obtain the UDPGalNAc.

The filter paper used in this invention may be commercially available one and is preferably thick one in view of the amount of material to be treated. The amount of nucleotide coatable on each filter paper is in the range of 10-300 mg, preferably 20-100 mg. If the material is coated in an excessive amount, tailing and the like will be caused thereby making the separation insufficient. The solvents for developing may be usual ones which may be used for nucleotide filter paper chromatography. The developing method may be an ascending method or a descending method with the latter being preferred for shortening of the time. The UDPGalNAc portion on the filter paper may be easily extracted with water.

As explained above in detail, the preparation process of this invention comprises the first step of enzymatically converting UDPGlcNAc in solution as the starting material to UDPGalNAc, the second step of treating the resulting reaction solution with UDPGlcNAc pyrophosphorylase thereby decomposing the UDPGlcNAc remaining in the reaction solution and the third step of separating the UDPGalNAc from the reaction solution.

The first step is characterized mainly by the use of a specific enzyme partially purified by means of ammonium sulfate fractionation, the second step characterized mainly by the direct use of UDPGlcNAc pyrophosphorylase without separating the sugar nucleotide from the reaction solution produced and the third step characterized mainly by the separation and purification of the UDPGalNAc in the reaction solution by paper chromatography. However, it is not always necessary to use these three steps in combination and one or two of them may be substituted by the conventional steps to obtain excellent effects or advantages of this invention as illustrated in the following Examples.

There will now be explained hereunder a method for measuring the activity of glycosyl transferase by the use of UDPGalNAc prepared by the process of this invention.

This method is used for measuring the activity of α-N-acetylgalactosaminyl transferase (hereinafter referred to as "A-transferase") which is glycosyl transferase participating in the biosynthesis of Type A blood substance found in plasma, human milk, stomach mucosa and the like. More particularly, it is a method which comprises treating Type O red blood cells with A-transferase in the presence of N-acetylgalactosamine donor thereby converting them to Type A red blood cells and then finding the activity of A-transferase from their strength of agglutination with anti A serum, characterized by using as the N-acetylgalactosamine donor a mixture of UDPGlcNAc and UDPGalNAc, the mixture being prepared by the conversion of UDPGlcNAc to UDPGalNAc using UDPGlcNAc-4-epimerase of *B. subtilis.*

The measurement of activity of A-transferase in serum or plasma is increasingly important since it is not only useful as a means for the detection and identification of mutation blood when it is difficult to determine the type (blood grouping), but also associated with glycolysis accompanying leukemia and cancer.

The heretofore known methods for measuring the activity of A-transferase are illustrated as follows:

(1) A method comprising reacting Type O red blood cells with enzyme and UDPGalNAc in attempts to convert them to Type A red blood cells and determining the extent or degree of conversion from their strength of agglutination with anti A serum; and (2) A method comprising reacting a soluble sugar acceptor such as 2-fucosyl lactose with a sugar donor labelled with enzyme and isotope and measuring the isotope level transferred to the acceptor.

However, the method (2) using isotope is unsuitable for daily inspection from the view-point of handling, cost and the like, while the method (1) is not put to practical use because of difficulties in obtaining UDPGalNAc as the substrate although it can be conveniently used in ordinary laboratories and inspection rooms.

There is known a process for the organic synthesis of UDPGalNAc [J. Biol. Chem. 253, 377–379 (1978)], however, it is impossible to produce UDPGalNAc in large amounts and at low costs by such a known process.

The present inventors made studies of processes for the preparation of UDPGalNAc which may conveniently be used as a substrate for A-transferase and, as a result of their studies, they found that measurement of the activity of A-transferase by the method (1) is possible even in a case where is used a crude UDPGalNAc preparation to which UDPGlcNAc has been enzymatically converted.

The object of the measuring method according to this invention is to provide a method for measuring the activity of A-transferase using UDPGalNAc, enzymatically converted from UDPGlcNAc, as the substrate without purifying the thus enzymatically produced crude UDPGalNAc.

This measuring method is a method for the measurement of the activity of A-transferase using a reaction of conversion of Type O red blood cells to Type A red blood cells, characterized by the direct use of a reaction solution in which UDPGlcNAc as the substrate has been enzymatically converted to UDPGalNAc.

The measuring method according to this invention will enable measurement of the activity of A-transferase, which has heretofore been difficult to carry out, to be effected conveniently and at a low cost even in inspection rooms and laboratories.

Attention is paid to measurement of the activity of A-transferase as a means for the identification of blood types, such as A sub-group and Bombay type, which are difficult to determine. It takes 2–3 days to determine blood types by heretofore generally used methods such as a dissociation test, while it takes only 2–3 hours by measuring the activity of A-transferase in accordance with the method according to this invention. This shows the great effects or advantages of this invention.

This invention will be better understood by the following Examples and Comparative Examples.

EXAMPLE 1

*Bacillus subtilis* IFO 3007 was cultivated in a nutrient medium consisting of 0.8% of peptone, 0.3% of yeast extract, 0.1% of glucose and 0.5% of sodium glutaminate. After the end of the cultivation, the cells produced were collected by centrifugation, suspended in 50 mM of a tris-hydrochloric acid buffer solution (pH: 7.5) containing 10 mM of magnesium chloride and 1 mM of ethylenediamine tetraacetic acid and then ruptured by subjecting to supersonic treatment. After removal of the cell debris by centrifugation, the resulting cell free extract was incorporated under agitation with powdered ammonium sulfate in such an amount that a 40% saturated concentration thereof was obtained. The resulting precipitate was removed by centrifugation to obtain a supernatant solution which was further incorporated with powdered ammonium sulfate to an extent that a 80% saturated concentration thereof was reached. The precipitate produced was collected by centrifugation, dissolved in the buffer solution and dialyzed to obtain an ammonium sulfate-fractionated preparation. The thus obtained preparation was added to 700 μmol of UDPGlcNAc, 7 mmol of tris-hydrochloric acid buffer solution (pH: 8.0), 700 μmol of magnesium chloride and 70 μmol of ethylenediamine tetraacetic acid, to form a mixture which was reacted at a temperature of 37° C. for 90 minutes. After suspension of the reaction, the nucleotide component was separated from the solution by adsorption and desorption thereof with activated carbon thereby to obtain a mixture of UDPGlcNAc and UDPGalNAc. The thus obtained mixture was treated with UDPGlcNAc pyrophosphorylase prepared from bakers' yeast to decompose the UDPGlcNAc into uridine triphosphate (UTP) and GlcNAc-1-phosphoric acid, after which the UDPGalNAc in the reaction solution was subjected to adsorption-desorption treatment with activated carbon and to ion-exchange chromatography [Dowex 1×2 (Cl⁻ type)] thereby to purify the UDPGalNAc. The amount of UDPGalNAc obtained was 138 μmol and the yield thereof against the UDPGlcNAc was 19.7%.

COMPARATIVE EXAMPLE 1

*B. subtilis* IFO 3007 was cultivated in the same manner as in Example 1 and the cells obtained were subjected to supersonic treatment to rupture them thereby obtaining a cell free extract. The thus obtained extract was used as the enzymatic preparation to convert the UDPGlcNAc to UDPGalNAc in the same manner as in Example 1, with the result that 60 μmol of UDPGalNAc was obtained from 465 μmol of UDPGlcNAc in a yield of 13%.

COMPARATIVE EXAMPLE 2

In the same manner as in Example 1, the reaction was carried out using as the enzymatic source a cell free extract prepared from *B. subtilis* IFO 3009. The result was that 100 μmol of UDPGalNAc was obtained from 1000 μmol of UDPGlcNAc in a yield of 10%.

EXAMPLE 2

A reaction solution containing 1 mmol of UDPGlcNAc, 10 mmol of a tris-hydrochloric acid buffer solution (pH: 8.0), 1 mmol of magnesium chloride and 0.1 mmol of ethylenediamine tetraacetic acid, was mixed with UDPGlcNAc-4-epimerase prepared from *B. subtilis*. The resulting mixture was reacted at 37° C. for 90 minutes, heated in a boiling bath for several minutes to suspend the reaction and freed of the precipitate by centrifugation. The supernatant solution thus obtained was incorporated with 7 mmol of sodium pyrophosphate, incorporated with UDPGlcNAc pyrophosphorylase prepared from bakers' yeast, and reacted at 30° C. for 6 hours to decompose the remaining UDPGlcNAc into UTP and GlcNAc-1-phosphate. Thereafter, the UDPGalNAc which was the end product, was separated from the other ingredients in the reaction solution and purified by subjecting the solution to operations such as adsorption-desorption treatment with activated carbon and chromatography using an ion-exchange resin. The amount of UDPGalNAc thus obtained was 154 μmol and the recovery rate obtained from the epimerized reaction solution was 60.2%.

COMPARATIVE EXAMPLE 3

One mmol of UDPGlcNAc was converted to UDP-GalNAc using epimerase of *B. subtilis* in the same manner as in Example 2. After the suspension of the reaction, the nucleotide was removed from the solution by subjecting to adsorption-desorption treatment with activated carbon in accordance with the conventional method thereby obtaining a mixture of UDPGlcNAc and UDPGalNAc. The subsequent operations were performed in the same manner as in Example 2, with the result that 120 μmol of UDPGalNAc was obtained from the epimerized reaction solution in a yield of 47%.

EXAMPLE 3

1400 μmol of UDPGlcNAc was subjected to the action of UDPGlcNAc-4-epimerase in the presence of magnesium chloride and ethylenediamine tetraacetic acid in a tris-hydrochloric acid buffer solution (pH: 8.0) thereby to obtain a mixture of UDPGalNAc and UDPGlcNAc. The thus obtained mixture was treated with UDPGlcNAc pyrophosphorylase prepared by bakers' yeast, in the presence of pyrophosphoric acid thereby to decompose the UDPGlcNAc into UTP and GlcNAc-1-phosphate. The reaction was suspended by heating and the resulting precipitate was removed by centrifugation, thus obtaining a supernatant solution. The thus obtained supernatant solution was concentrated and incorporated with manganese chloride to precipitate pyrophosphoric acid and remove it from the solution. The solution so treated was further concentrated, after which nucleotide was coated in band form in an amount of about 100 mg on each thick filter paper. The nucleotide was developed with a developing solvent consisting of 95% ethanol: 1 M ammonium acetate=7.5:3 (v/v) and, thereafter, the UDPGalNAc portion on the filter paper was detected by absorption of ultraviolet rays, cut off from the filter paper and then extracted with water. The amount of UDPGalNAc obtained was 17 μmol and the recovery rate was 90%.

COMPARATIVE EXAMPLE 4

1650 μmol of UDPGlcNAc was treated with pyrophosphorylase in the same manner as in the Examples and then subjected to adsorption with activated carbon and ion-exchange chromatography thereby to separate and purify the UDPGalNAc. The amount of UDPGalNAc obtained was 228 μmol and the recovery rate was 61%.

EXAMPLE 4

A reaction solution containing 1.4 mmol of UDPGlcNAc, 14 mmol of a tris-hydrochloric acid buffer solution (pH: 8.0), 1.4 mmol of magnesium chloride and 0.14 mmol of ethylenediamine tetraacetic acid, was incorporated with UDPGlcNAc-4-epimerase prepared from *B. subtilis* IFO 3007 in the same manner as in Example 1 and then reacted at 37° C. for 90 minutes. The reaction solution so treated was heated in a boiling water bath for several minutes to suspend the reaction and freed of the precipitate by centrifugation thereby to obtain a supernatant solution which was then treated directly with UDPGlcNAc pyrophosphorylase to decompose the remaining UDPGlcNAc into UTP and GlcNAc-1-phosphoric acid. The reaction solution so decomposed was treated in the same manner as in Example 3 to separate the UDPGalNAc therefrom for purification. The amount of purified UDPGalNAc obtained was 419 μmol.

EXAMPLE 5

A crude UDPGalNAc preparation used in this invention may be prepared as follows. One mmol of UDPGlcNAc was mixed with UDPGlcNAc-4-epimerase enzyme prepared from *B. subtilis*, in the presence of 10 mM of MgCl$_2$ and 1 mM of EDTA in an 0.1M tris-hydrochloric acid buffer solution (pH: 8.0). The resulting mixture was reacted at 37° C. for 90 minutes. After the end of the reaction, the mixture so reacted was heated in a boiling water bath for several minutes to suspend the reaction, cooled and then centrifuged at 10,000×g for 10 minutes to obtain a supernatant solution which was deemed to be a crude UPDGalNAc preparation.

There will be explained hereunder an example of measurement of the activity of A-transferase in serum using said the crude UPDGalNAc.

0.2 ml of a cacodylate buffer solution (pH: 6.5) and 0.5 ml of Type A serum (containing A-transferase to be tested for activity) were introduced into a test tube and then incorporated with 0.1 ml of the crude UPDGalNAc to form a mixture. The thus formed mixture was preliminarily heated to 37° C. for 5 minutes. The mixture so heated was incorporated with 0.05 ml of a 50% solution of Type O red blood cells and then reacted under oscillation at 37° C. for 2 hours. After the end of the reaction, the entire material was washed twice with a physiological saline solution to stop the reaction and suspended in 1 ml of the same solution. When the resulting suspension was treated with anti A serum which had been subjected to serial dilutions, it was found that coagulation occurred as far as the dilution was increased 64 times.

COMPARATIVE EXAMPLE 5

In the same manner as in Example 5, A-transferase was measured for its activity using isolated and purified UDPGalNAc in place of the crude UDPGalNAc preparation as the substrate for reaction. Even in a case where the purified UDPGalNAc was used, coagulation with anti A serum occurred as far as the dilution was increased 64 times as in Example 5.

This showed that such a crude UPDGalNAc preparation is satisfactory for use as a substrate for measurement of the activity of A-transferase.

What is claimed is:

1. In the method of measuring the activity of α-N-acetylgalactosaminyl transferase wherein Type O red blood cells are converted to Type A red blood cells in the presence of a N-acetylgalactosamine donor and the activity of A-transferase is determined on the basis of their strength of agglutination with anti A serum, the improvement wherein the N-acetylgalactosamine donor which is the substrate for the conversion is a reaction mixture obtained by the conversion of uridine diphosphate-N-acetylglucosamine to uridine diphosphate-N-acetylgalactosamine in the presence of uridine diphosphate-N-acetylglucosamine-4-epimerase obtained by partially purifying cell free extracts of *Bacillus bacterium* by fractionation with ammonium sulfate, the reaction mixture being composed mainly of the uridine diphosphate-N-acetylgalactosamine and unreacted uridine diphosphate-N-acetylglucosamine.

2. The method according to claim 1 wherein the molar ratio between said uridine diphosphate-N-acetylglucosamine and said uridine diphosphate-N-acetylgalactosamine is 65:35 in the equilibrium solution.

* * * * *